US006888639B2

(12) United States Patent
Goebel et al.

(10) Patent No.: US 6,888,639 B2
(45) Date of Patent: May 3, 2005

(54) IN-SITU FILM THICKNESS MEASUREMENT USING SPECTRAL INTERFERENCE AT GRAZING INCIDENCE

(75) Inventors: Andreas Goebel, Summit, NJ (US); Moshe Sarfaty, Cupertino, CA (US); Sebastien Raoux, San Francisco, CA (US)

(73) Assignee: Applied Materials, Inc., Santa Clara, CA (US)

( * ) Notice: Subject to any disclaimer, the term of this patent is extended or adjusted under 35 U.S.C. 154(b) by 480 days.

(21) Appl. No.: 09/963,048

(22) Filed: Sep. 24, 2001

(65) Prior Publication Data

US 2003/0090676 A1 May 15, 2003

(51) Int. Cl.[7] .............................. G01B 11/02; G01B 9/02
(52) U.S. Cl. ........................ 356/504; 356/491; 356/492; 356/496; 356/499; 356/503
(58) Field of Search ................................. 356/504, 491, 356/492, 496, 499, 503

(56) References Cited

U.S. PATENT DOCUMENTS

| | | | |
|---|---|---|---|
| 5,045,149 A | | 9/1991 | Nulty |
| 5,846,373 A | * | 12/1998 | Pirkle et al. ............ 156/345.25 |
| 6,081,334 A | * | 6/2000 | Grimbergen et al. ....... 356/499 |
| 6,207,008 B1 | | 3/2001 | Kijima |
| 6,264,852 B1 | * | 7/2001 | Herchen et al. .............. 216/60 |
| 6,322,714 B1 | * | 11/2001 | Nallan et al. .................. 216/67 |
| 6,358,359 B1 | * | 3/2002 | Peinador et al. ............ 156/345 |

FOREIGN PATENT DOCUMENTS

| | | |
|---|---|---|
| EP | 1 111 358 A2 | 6/2001 |
| WO | WO 01/24255 A2 | 4/2001 |

OTHER PUBLICATIONS

Angell et al., "Grazing angle optical emission interferometry for end–point detection," *Applied Physics Letters*, 58(3):240–242 (1991).

Sarfaty et al., "Real–Time Monitoring and Control of Plasma Etching," *Japanese Journal of Applied Physics*, 37(48):2381–2387 (1998).

Benson et al., "In–situ Spectroscopic Reflectometry for Polycrystalline Silicon Thin Film Etch Rate Determination During Reactive Ion Etching," *Journal of Electronic Materials*, 25(6):955–964 (1996).

Killeen et al., "In Situ Spectral Reflectance Monitoring of III–VEpitaxy," *Journal of Electronic Materials* , 33(2):179–183 (1994).

Laaksonen, "Full Water Inusforcemetric Measurements of Etch and Trictnocc Uniformity," Semiconductor Inferrational, pp. 277–286 (1997).

Tepermeister et al., "In situ monitoring of product wafers," Solid State Technology, pp. 83–86 (1996).

* cited by examiner

*Primary Examiner*—Gregory J. Toatley, Jr.
*Assistant Examiner*—Khaled Brown
(74) *Attorney, Agent, or Firm*—Townsend and Townsend and Crew (57) ABSTRACT

A method and system using spectral interference of light from plasma emissions collected at near grazing incidence to in-situ monitor and control the film thickness of a non-opaque film. Embodiments of this invention are particularly useful to all substrate processing chambers equipped to form an in-situ plasma within the chamber and which are used to deposit or etch non-opaque films. One embodiment of the method of the present invention forms a plasma within a substrate processing chamber to deposit a non-opaque film on a wafer substrate within the chamber. During the plasma deposition process, a plurality of wavelengths of radiation including those reflected from the top and bottom layer of the film being deposited upon a wafer surface are collected through an existing viewport, and conveyed to a spectrometer for measurements via an optical fiber attached near this viewport. These measurements are analyzed to determine the film's thickness. An alternate embodiment of the method of the present invention uses an interference filter to confine the spectral composition of the plasma emissions to an emission at a narrow wavelength interval and a photodiode to detect the intensity of the emission.

24 Claims, 5 Drawing Sheets

IN-SITU FILM THICKNESS MEASUREMENT USING SPECTRAL INTERFERENCE AT GRAZING INCIDENCE

BACKGROUND OF THE INVENTION

The present invention is related to wafer processing and in particular to a method of monitoring a deposition or an etch process. More specifically, the present invention relates to a method of measuring the thickness of a film layer being deposited by a plasma enhanced chemical vapor deposition process (PECVD) or etched by a plasma etch process. The present invention may be used to measure the deposition or etch rate and film thickness of a variety of optically transparent films.

To provide repeatable device performance, the thickness of film layers must be maintained within specified tolerances. One methodology for determining the thickness of a film layer being deposited is to time the deposition and factor the time period with a theoretical rate to approximate the film thickness. To establish the actual deposition rate in a chamber, a semiconductor manufacturer processes and subsequently measures a film deposited on a few test wafers. The film thickness on actual production wafers is then assumed to approximately equal the measured deposition rate times the processing time. This process is time consuming and potentially results in wafers that do not meet the production specifications, as process drift may result in variable deposition rates.

Additionally, present process control is performed between two process steps. For example, a deposited film's properties such as thickness, stress, refractive index (RI), uniformity, and etch rate, which are important parameters characterizing the quality of a dielectric layer, are measured on a number of test wafers after the deposition or the etching of the layer on the test wafers. These test wafers are processed within a group of production wafers in order to assess whether the process step was performed within the desired specification for the entire group of wafers from which the test wafers were selected. This method can result in a substantial waste, since deviations from desired process parameters, and thus the production of film layers having non-optimal or undesirable properties, are only detected after a whole group of wafers has been processed. An additional limitation of the current test wafer thickness monitoring is that it is only capable of disclosing whether a particular film layer possesses the correct thickness, not why a film layer might deviate from a desired thickness. Accordingly, periodic process quality assessment methods are not equipped to provide information regarding potential counter measures to take to bring a process back in compliance with specifications. Therefore, a need to develop an in-situ characterization and process control exists.

Various in-situ systems for measuring deposition or etch rates have been developed by several research organizations and semiconductor manufacturers. These include single wavelength reflectometers, single wavelength ellipsometers, spectral ellipsometers, and optical emission interferometers. In these methods and systems, etch rate, deposition rate, rate uniformity and hence film thickness and variations thereof are calculated from the observed periodic modulations in the reflected light intensity. The origins of the modulations in the reflected light intensity and changes in its polarization arise from interference caused by the relative phase shift in the light reflected from the top and the bottom of the thin film. Systems employing light interference to measure deposition and etch rates typically include a light source and a detector and analyzer to detect and analyze the reflected light. The light detection can be either monochromatic (single wavelength) or spectral, and it can be carried out by many types of light sensors. Typically light from an optical source is conveyed to the detection equipment via an optical fiber. One class of these in-situ systems relies on optical emission interferometers (OEI) to monitor the wafer state during film deposition. OEI use light from the plasma as the source of incident radiation (i.e., the source of light upon the wafer), thereby reducing the cost and complexity of the wafer state monitor system. Other methods use an external light source along with or in lieu of the plasma emissions as the source of light upon the wafer.

However, most of these methods and systems require the source of incident radiation to be preferably perpendicular to the wafer surface. This also requires the detection equipment to be arranged in a manner to receive the reflected light, which is also nearly perpendicular to the wafer surface. This perpendicular or near perpendicular incidence requires the light source and detection equipment to be located opposed to the substrate's upper surface, which is typically reserved for other chamber components. Such a requirement may necessitate modifications to the design and geometry of some substrate processing chambers. Although some have been able to extend their system's angle of incidence (for detection) to as high as 52 degrees (measured with respect to wafer surface normal), such a setup still requires a large space between the inner top surface of the chamber and the wafer, to allow the reflected light to reach a detector.

Further, these geometric constraints that may require modifications to the chamber design, are further compounded by the needs of some existing systems to use expensive and complicated optical lens systems to gather and direct the light to the detection and analysis equipment.

Therefore, there is a need to develop a cost effective and easily implementable system for in-situ characterization and control of etch and deposition processes.

SUMMARY OF THE INVENTION

Spectral interference of light from plasma emissions collected at near grazing incidence is used to provide in-situ monitoring of film thickness in a plasma enhanced chemical vapor deposition (PECVD) or an etch process. Embodiments of this invention are particularly useful to substrate processing chambers equipped to form an in-situ plasma within the chamber and which are used to deposit or etch non-opaque films. As referred to herein, a PECVD process refers to any CVD process where the substrate processing chamber is equipped to form an in-situ plasma within the chamber. Moreover, as referred to herein, non-opaque films are those films that are non-opaque at least to some of the wavelengths of light emitted by the plasma.

One embodiment of the method of the present invention works with a process that forms a plasma within a substrate processing chamber to deposit a non-opaque film on a wafer substrate within the chamber. During the plasma deposition process, a plurality of wavelengths of radiation including those reflected from the top and bottom surfaces of the film deposited upon the wafer are collected at near grazing incidence through an existing viewport, and conveyed to a spectrometer for measurements via an optical fiber attached near this viewport. The angle of incidence is measured with respect to the wafer surface normal and near grazing angles of incidence are angles in the range of 80 to less than 90 degrees. These acquired spectra are analyzed to determine the film deposition rate and thickness.

An additional embodiment of the method of the present invention uses an interference filter to confine the spectral composition of the plasma emissions to an emission at a narrow wavelength interval and a photodiode to detect that emission. An advantage of this embodiment is the reduction in cost and the improved signal to noise ratio obtained by using a narrow wavelength interval and by not using a spectrometer.

These and other embodiments of the preset invention are described in more detail in conjunction with the text below and attached figures.

DESCRIPTION OF THE SPECIFIC EMBODIMENTS

Figure 1:
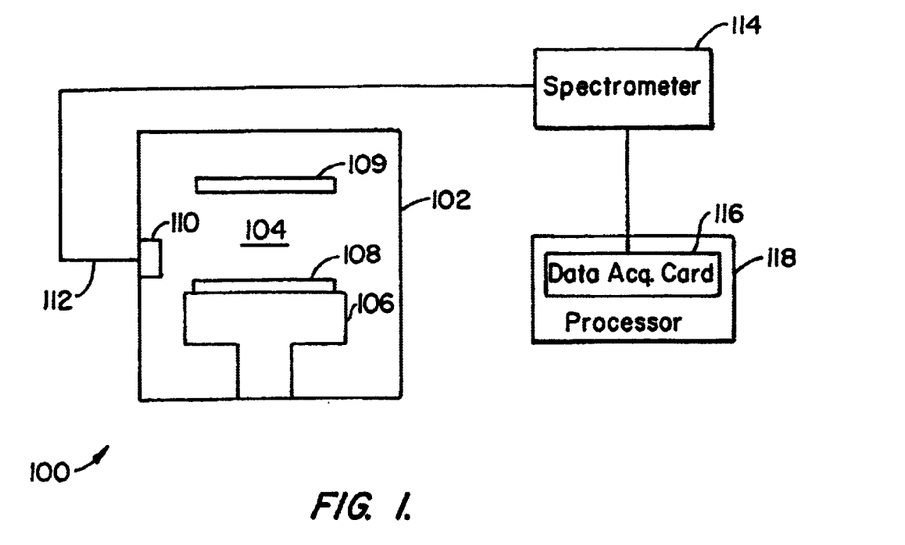
FIG. 1 is a simplified cross-sectional view of an exemplary plasma deposition chamber configured to practice one embodiment of the method of the present invention.

I. An Exemplary Plasma Enhanced Chemical Vapor Deposition (PECVD) Chamber Configured to Practice the Present Invention The method of the present invention can be used with any standard plasma deposition chamber that includes a side-view window or side-viewport through which plasma emissions reflected off the surface of the wafer can be directed to a light detection and analysis device. In one embodiment, the light detection device can be a spectrometer. FIG. 1 is a simplified cross-sectional view of an exemplary PECVD chamber 100 configured to practice the method of the present invention. As shown in FIG. 1, PECVD chamber 100 includes a housing 102 that surrounds a substrate processing region 104. During a deposition process a substrate 108 is supported on a pedestal 106 and exposed to a plasma formed in region 104. The plasma generates electromagnetic radiation that includes emissions having wavelengths in the optical spectrum (i.e., from 200 nm to 900 nm). A portion of these emissions are reflected from the top and bottom of the film deposited on the substrate 108 and through a window 110 and into a fiber optic cable 112. The fiber optic cable has an optical acceptance angle to ensure that the fiber is collecting light reflected from the film being deposited on a wafer. A fiber optic cable having a too narrow optical acceptance angle may not be capable of collecting light which has been reflected from the wafer being processed. In the setup described herein, the fiber optic cable has a 50 degree optical acceptance cone. The light which has been collected by the fiber optic cable travels through the fiber optic cable 112 to the spectrometer 114.

One key difference between the chamber 100 and previously known chambers is the placement of the window 110 relative to the pedestal 106 and substrate 108. The preferred position for window 110 is above the wafer 108 and in chambers that have an upper electrode, to the side and below the upper electrode 109. This window placement is different from other methods of light detection that use interference from near orthogonal (to the wafer) incidence of light, which require that the detector be placed higher or even directly above the pedestal.

The present inventors discovered that optical interference (e.g., interference fringes) which stem from the superposition of light reflected from the top 314 and bottom 316 interface of a film (shown in FIG. 3) on a wafer at a nearly grazing angle of incidence can be observed. The near grazing angle of incidence condition, i.e., at least 80 and less than 90 degrees with respect to the substrate normal, results in a strong attenuation of the reflected light. This is due to strong internal reflection of that light at the top interface of the film which was previously reflected from the bottom interface. However, the inventors have discovered that the remaining interference intensity is still sufficient for the characterization of layer material properties and production parameters. In comparison, other typical interference-based methods use setups in which light emission and collection are closer to orthogonal incidence with respect to the substrate.

The spectrometer 114 diffracts the collected light by a planar grating (not shown). The spectrum is then projected onto a 1-dimensional linear charge-coupled device (CCD) array and its intensity distribution is recorded. In one embodiment, spectrometer 118 is an OceanOptics spectrometer using grating #1, which has 600 lines/mm. The data is transmitted to the processor 118 through the data acquisition card 116. The data acquisition card 116 coupled to the processor 118 collects data representing the separated wavelengths at a periodic sampling rate. The processor 118 is used to monitor and/or control the deposition or etch process by comparing the in-situ interference data with predetermined settings.

The embodiments of the present invention provide several advantages. First, as discussed above, the obvious position for the optical fiber when using close to normal incidence is within the shower head, thus requiring modifications to the chamber hardware. The implementation of interferometry at near grazing incidence circumvents the need to change the chamber's design or geometry, in order to accommodate the placement of the optical fiber.

Second, by using such a grazing angle of incidence and employing the large acceptance angle of an optical fiber, one is able to observe large portions of the wafer surface without having to use complicated optical lens systems, or complicated multi-region systems and their associated data averaging algorithms. The method of the present invention inherently provides a spatially averaged deposition rate and film thickness data at low system costs, because the light received by the detector does not need to emanate from a clearly defined spot on the wafer.

Additionally, this embodiment decomposes the light received into its spectral components using a spectrometer.

This provides measurements of optical emissions and their associated interference at many wavelengths at the same time. With multi-wavelength detection, the entire spectrum may be used for control monitoring, or, if appropriate, a few selected wavelengths that have been determined to be most sensitive to a particular process may be used. In addition, this method potentially has more flexibility for wide application to a variety of different processes—because it uses multiple wavelengths. Furthermore, the simultaneous observation of many spectral lines results in a more reliable value for the deposition rate and film thickness because the results obtained for each line can be compared against each other. Simultaneous observations of many spectral lines provide more data for subsequent analysis, and thus enable an increased measurement reliability.

In an alternate embodiment, the spectrometer is replaced by a photodiode. In this alternate embodiment, the light detection equipment consists of an interference filter placed in between the chamber window 110 and the fiber optic cable 112 to confine the spectral composition of the plasma emissions to an emission at a narrow wavelength interval and a photodiode to detect the intensity of that emission. Since a photodiode is used to detect the optical emissions, instead of a spectrometer, this alternate embodiment allows for further reductions in the overall cost and complexity of the system.

II. Description of a PECVD Process Monitored According to an Embodiment of the Present Invention A PECVD process to deposit silicon dioxide on a substrate was monitored in a chamber configured as described above. During the deposition, a portion of the light which is emitted from the plasma and reflected from the wafer surface at an angle of incidence of approximately 80 to less than 90 degrees (as measured from a line perpendicular to the wafer's deposition receiving surface) is collected. The light is acquired through the side viewport window of a chamber by an optical fiber. The intensity of the light's spectral components is then recorded.

Figure 2:
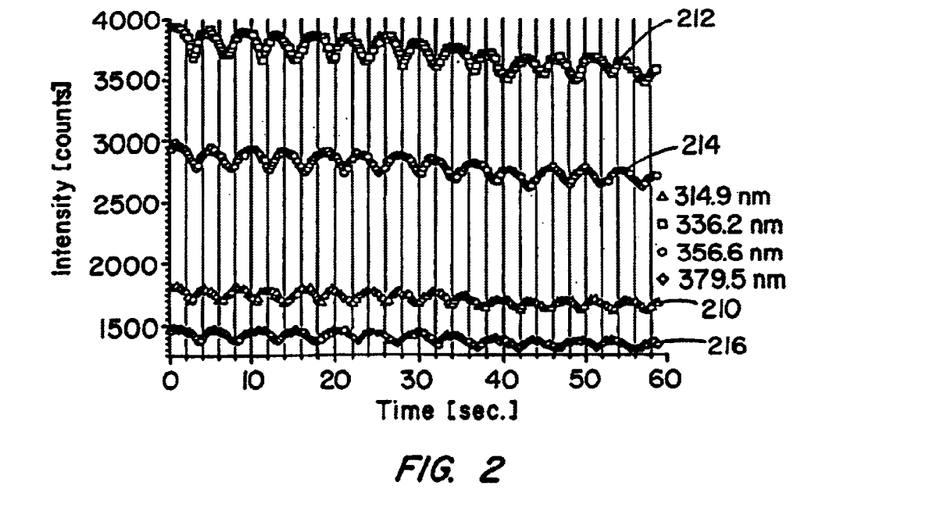
FIG. 2 is a plot of the time dependent plasma emissions for different wavelengths during the PECVD of silicon dioxide in an Applied Materials 300 mm Producer system.

Using a setup similar to that of FIG. 1 and described above, an example of data obtained during a PECVD deposition process of a 1.2 mm thick silicon dioxide film is shown in FIG. 2, which shows oscillations in the peak intensities of several plasma emission lines at wavelengths: 314.9 nm, 336.2 nm, 356.6 nm and 379.5 nm, indicated by reference numbers 210, 212, 214 and 216 respectively. These wavelengths represent strong emissions due to the excitation of $N_2$ molecules in the plasma, which are characteristic of the particular recipe used during the deposition of silicone dioxide. Furthermore, FIG. 2 shows that the oscillation period is shorter for shorter wavelength emissions. For example, as shown on FIG. 2, the oscillation period for the 314.9 nm wavelength emission (210) is less than 4 seconds, while the oscillation period for the 379.5 nm wavelength emission (216) is more than 4 seconds. Another way of observing the shorter oscillation period for shorter wavelength emissions is by a visual inspection of plasma emission lines of FIG. 2, which shows that the shorter (210) wavelength emissions go through 13 full cycles, while the longer (216) wavelength emissions go through 11 full cycles in the 60 second interval. When analyzed in detail, the oscillation frequency is inversely proportional to the wavelength $\lambda$, as is expected for interference phenomena.

Figure 3:
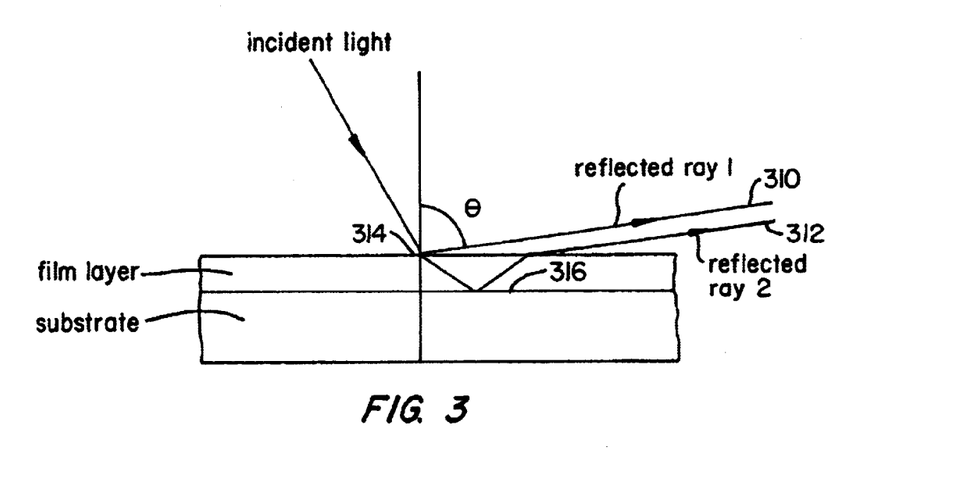
FIG. 3 is a simplified diagram describing the interference model showing light being reflected from the top and bottom of a transparent layer.

FIG. 3 provides the basis for explaining the interference condition at the grazing angles of the present invention. This figure (FIG. 3) shows light is reflected from a thin transparent film on the surface of the substrate. The two reflected beams as indicated by reference numbers 310 and 312 have a phase difference because of the difference in their optical paths and the differences in optical densities of the film and the substrate. During film deposition, the thickness of the film changes, causing a change in the phase difference and therefore a change in the signal detected by the light detection equipment. Although the phase difference changes monotonously, the signal intensity will vary periodically since the intensity depends only on the $2\pi$-modulus of the phase difference between the two beams reflected from top and bottom surface of the film. The periodicity of the intensity of the optical emissions (i.e., the minima and maxima of the optical emissions) is dependent on the phase difference, $\delta$, which is in turn dependent on the rate of change of the thickness of the film layer (being deposited) and ultimately on the deposition rate, as is further described below.

During film deposition, the film thickness d varies as a function of time. As a result, periodic fluctuations in intensity (due to optical interference) of the light collected at grazing incidence are observed as shown in FIG. 2. The variation in the collected signal intensity is due to the interference of light reflected from the top and bottom of the thin film as the film thickness changes. To determine the deposition rate, an in-situ system's data analysis software can be used to process this data by counting each oscillation and determining the time interval between the oscillations and by using a correlation between each oscillation and an incremental film thickness.

The rate of occurrence of the intensity oscillations (i.e., rate of occurrence of maxima or minima in the emission lines of FIG. 2) can be called interference fringe frequency v. It is synonymous with the rate of change of the relative phase shift $\delta$ with respect to time, i.e., $\Delta\delta/\Delta t$ and directly related to the film deposition rate. As the film thickness being deposited increases, there is a corresponding shift in optical interference of the light being reflected from the top and bottom of the film layer, because the position of the upper reflecting surface is changing as the film layer's thickness increases.

The interference fringe frequency can be either the number of maxima or minima in the emission lines observed per unit time as shown on FIG. 2. These maxima and minima occur at the rate at which the phase difference $\delta$ between the rays reflected from the top surface of the film and those reflected from its bottom equals $2n\pi$ or $(2n+1)\pi$, respectively, where n is an integer. The fundamental equation for the phase difference $\delta$ is given in equation 1 below:

$$\delta = [4\pi n_f/\lambda] d \cos \theta_f \qquad \text{Eqn. 1}$$

where:
$\delta$ is the phase difference;
$n_f$ is the wavelength dependent refractive index;
$\theta_f$ is the angle between the normal of the surface and the beam within the layer as depicted in FIG. 3; and
d is the layer thickness.

Therefore, for a given $\theta_f$ the fringe frequency v is inversely proportional to the wavelength $\lambda$ and proportional to the refractive index $n(\lambda)$, i.e., equation 2 holds $$v = \Delta\delta/\Delta t = (4\pi n_f/\lambda)(\Delta d/\Delta t) \cos \theta_f, \text{ or}$$

$$v \sim n_f(\lambda)/\lambda \qquad \text{Eqn. 2}$$

Where
v is the interference fringe frequency;
$n_f(\lambda)$ is the wavelength dependent refractive index; and
$\lambda$ is the wavelength.

Figure 4:
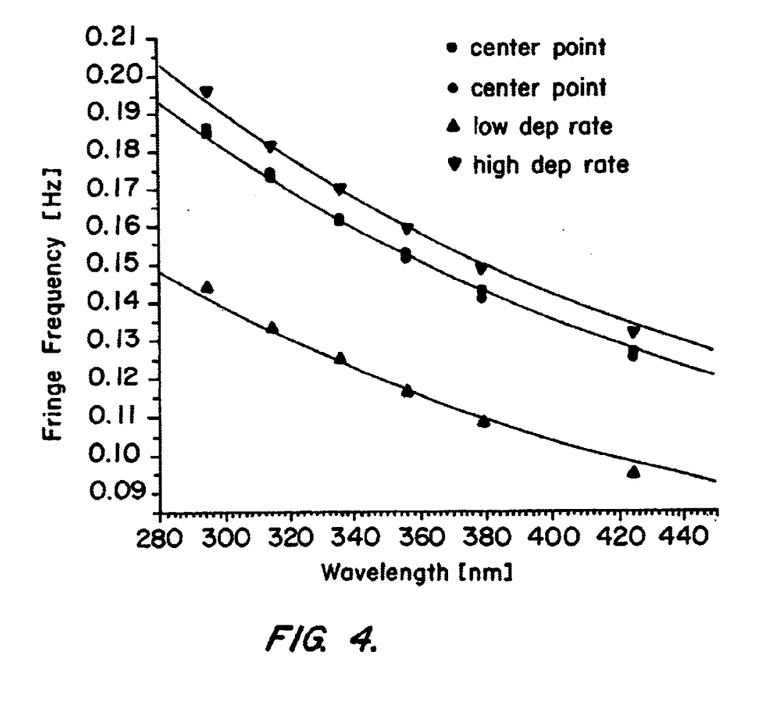
FIG. 4 is a plot of fringe frequency versus wavelength obtained for four wafers during a silicon dioxide deposition process using various recipes.

Actual experimental measurements taken from films deposited using various recipes show that the observed fringe frequencies obey this rule. FIG. 4 shows this dependence of the interference fringe frequency on wavelength for several cases, namely: (i) for two wafers for which the center point recipe (best known method) was used and cases in which a (ii) a higher and (iii) a lower deposition rate recipe were used. The solid lines are the results of curve fits to the data by using Eqn. 2, i.e., the inverse wavelength rule for interference fringes. The good agreement between the curve fits and Eqn. 2 suggests that the deposition rate can be accurately inferred from these observations. It is noted from Eqn. 2 that the fringe frequency v is related to the change in layer thickness through the refractive index of the film. This refractive index can be determined when analyzing Eqn. 2 for several wavelengths. In practice, however, it may be more advantageous to perform pre-production or calibration processes, as described below.

III. Description of a Calibration Process According to the Present Invention

During the pre-production or calibration run, the same measurements as described above are made, which provide a plot of the periodic fluctuations in intensity (due to optical interference) similar to those of FIG. 2. As discussed above, the in-situ measurement method determines film layer thickness by counting the periodic fluctuations in plasma intensity, where each oscillation represents a certain incremental film layer thickness.

Hence, a pre-production or calibration run may be performed to determine the relationship between actual measurements of layer thickness and measurement data provided by interference-based metrics (e.g., periodic fluctuations in intensity ). Therefore, one purpose of calibration is to determine for a given set of process parameters the relationship between periodic fluctuations in intensity and incremental layer thickness. Using the calibration information, a desired final deposited film thickness can be achieved by counting a predetermined number of oscillations during the deposition process. Likewise, a desired layer thickness can be etched by counting a predetermined number of oscillations during the etch process.

IV. Use of an Embodiment of the Present Invention to Monitor an Exemplary PECVD Silicon Nitride Deposition Process In order to better understand the method of the present invention, an example of the method used to monitor a film deposition process is presented below. This example is for illustrative purposes only and should not be considered as limiting to the claims. This example confirms the wide applicability of the method of the present invention to measure various types of film depositions. In this example, the deposition of silicon nitride using a center point recipe in an Applied Materials Producer 300 system PECVD chamber was monitored.

Figure 5A:
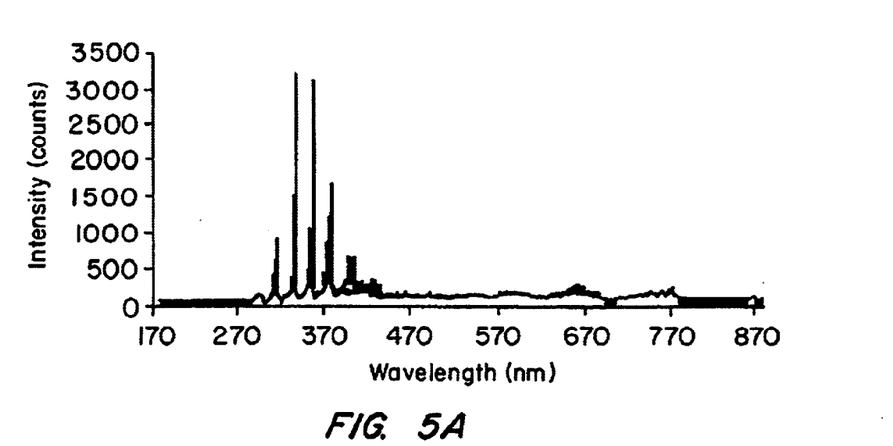
FIG. 5A is a plot of a full silicon nitride deposition spectrum.
Figure 5B:
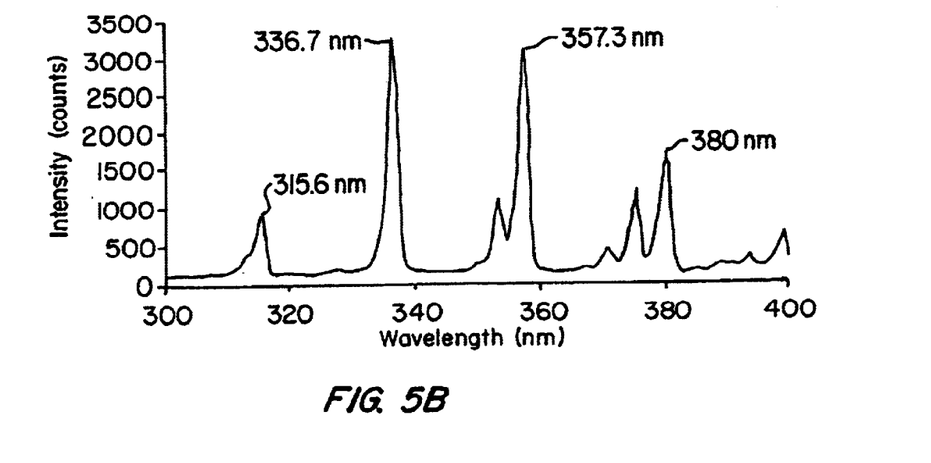
FIG. 5B is a close-up plot of wavelengths of interest from the silicon nitride deposition spectrum of FIG. 5A.

Using a center point recipe two different deposition intervals were applied, resulting in approximately 2880 Å and 1000 Å thick silicon nitride layers. During the deposition, the optical spectra were recorded for further analysis. All intensity measurements provided herein are based on the intensity values measured in volts, which are then digitized and displayed in "count units." In the description provided below, intensity value measurements of FIG. 5A show the full spectrum obtained for a test wafer (2880 Å layer case) at 45 seconds. FIG. 5B shows a close-up of FIG. 5A showing the four largest signal-to-noise ratio peaks. The four emissions at 315.6 nm, 336.7 nm, 357.3 nm and 380 nm are due to the excitation of molecular nitrogen in the plasma. The time-domain analysis of emissions from these four wavelengths is discussed below. In addition, an ex-situ film thickness measurement was also made.

Figure 6A:
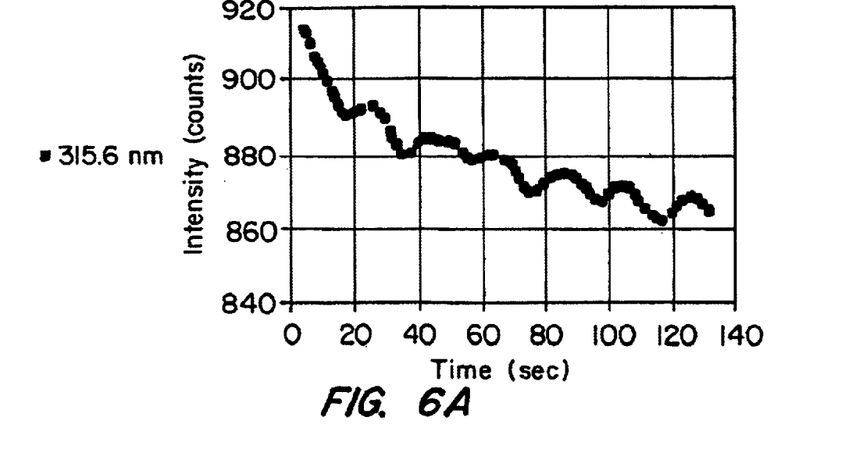
FIG. 6A is a plot of the time dependent plasma emission intensity for the 315.6 nm wavelength during the deposition of the silicon nitride layer of FIG. 5A.
Figure 6B:
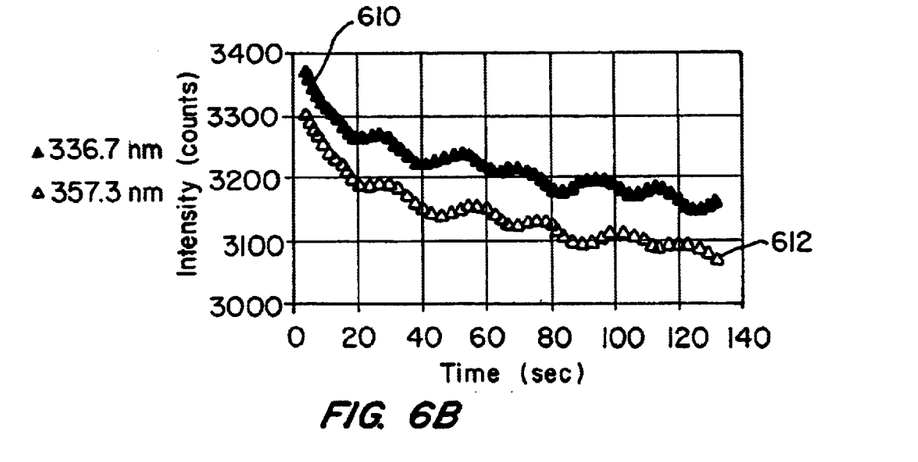
FIG. 6B is a plot of the time dependent plasma emission intensity for the 336.7 nm and the 357.3 nm wavelengths during the deposition of the silicon nitride layer of FIG. 5A.
Figure 6C:
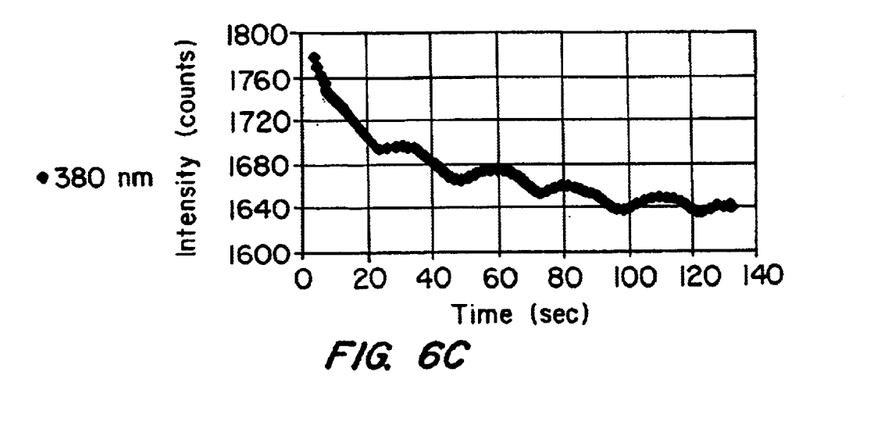
FIG. 6C is a plot of the time dependent plasma emission intensity for the 380 nm wavelength during the deposition of the silicon nitride layer of FIG. 5A.

Time-dependent periodic fluctuations in intensity for the four wavelengths described above are shown in FIGS. 6A–C. FIG. 6A shows the time dependent periodic fluctuations in intensity for the 315.6 nm wavelength during the deposition of silicon nitride. FIG. 6B shows the signal for the 336.7 nm and the 357.3 nm wavelengths, indicated by reference numbers 610 and 612 respectively, and FIG. 6C shows the signal for the 380 nm emission line. As can be seen from these figures more oscillations are observed for shorter wavelength emissions—in agreement with Eqn. 1 above. Similar interference-based periodic fluctuations in intensities were also obtained for the thin film wafers.

Figure 7:
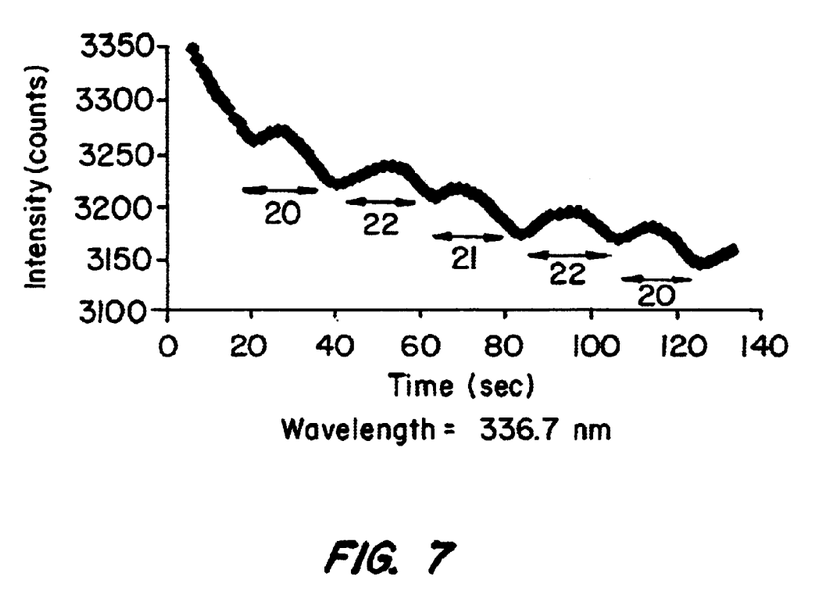
FIG. 7 is a plot of the time dependent plasma emission intensity for the 336.7 nm wavelength used for the analysis.

Each of the intensity recordings was then further examined for fringe analysis (fringe count method). Fringe analysis consists of counting the number of oscillations, determining fringe time interval (i.e., period), and thus the fringe frequency. Table 1 shows the results of fringe frequency calculations for a time dependent fringe profile at 336.7 nm of FIG. 7. Fringe time interval is measured at intensity minima because the trace is sharper at the minima. For this particular pattern a total of 5 fringe periods were measured as shown in FIG. 7 and Table 1, resulting in an average fringe frequency of 0.048 Hz with a standard deviation of 0.002 Hz (4.2%). Similar analyses are performed for each of the other three frequencies, and summarized in Table 2.

Results of Fringe Frequency Calculations at 336.7 nm

TABLE 1

| Minima (sec) | Fringe time (sec) | Frequency (Hz) |
| --- | --- | --- |
| 21 | | |
| 41 | 20 | 0.05 |
| 63 | 22 | 0.045 |
| 84 | 21 | 0.048 |
| 106 | 22 | 0.045 |
| 126 | 20 | 0.050 |
| Average | 21 | 0.048 |
| Std. Div. | 1 | 0.002 |

Table 2 below shows the results of fringe analyses for the four wavelengths that were analyzed. This table also shows the results from an ex-situ measurement. In one embodiment, to calculate deposition rate and total deposition layer thickness, first, periodic fluctuations in intensity are measured (e.g., as in FIGS. 6A–C). Next, for each wavelength the time difference between successive minima (or maxima) or measured and a period is determined, from which a fringe frequency is determined. For Example, fringe frequencies for the 315.6 nm, 336.7 nm, 357.3 nm and 380 nm are determined to be 0.0524 Hz, 0.0484 Hz, 0.0442 Hz and 0.0416 Hz respectively. Next, the deposition rate is determined to be equal to the fringe frequency times the "Thickness/fringe", which is obtained from a calibration run. For example, for measurements at a 315.6 nm wavelength emissions, the deposition rate is equal to 1346.3 Å/min (0.0524 Hz times 428.2 Å/fringe times 60 seconds/min). Total layer thickness is determined by integrating the deposition rate over the deposition duration, or alternately by multiplying the "Thickness/fringe" by the number of fringes (which correspond to the number of minima or maxima).

This table shows that the in-situ measurements for deposition rates agree quite favorably with the ex-situ measurements, since they are within the standard deviation of the ex-situ measurements. More particularly this table shows that the shortest wavelength which provides the highest number of periodic fluctuations in intensity (highest fringe frequency) may also provide for a better resolution of the wafer state. The fringe analysis for the 315.6 nm wavelength estimates an in-situ deposition rate of 1346.3 Å/min as compared to the ex-situ measured deposition rate value of 1344.9 Å/min. Alternately, an assessment of the agreement of in-situ measurements with ex-situ measurements may be made by comparing the difference between the average of the in-situ and the ex-situ measurements of deposition rate against the standard deviation of the ex-situ measurements. Here, the average in-situ measurement from all the measured wavelengths yields a value of 1326.73 Å/min which has a difference of 18.18 Å/min from the ex-situ measurement, which is less than the standard deviation of 29.2 Å, thus also showing a favorable agreement between the in-situ and ex-situ measurements.

Comparison of Ex-Situ Measurements vs. In-Situ Estimates for Thick Film Wafers

TABLE 2

| Metrics | Ex-Situ | In-Situ | | | |
|---|---|---|---|---|---|
| | | 315.6 nm | 336.7 nm | 357.3 nm | 380 nm |
| Average Thickness (Å) | 2869.1 | N/A | N/A | N/A | N/A |
| Fringe Frequency (Hz) | N/A | 0.0524 | 0.0484 | 0.0442 | 0.0416 |
| Deposition Rate (Å/min) | 1344.9 | 1346.3 | 1322.5 | 1311.9 | 1326.2 |
| Standard Deviation (Å) | 29.2 | N/A | N/A | N/A | N/A |
| Number of Fringes | N/A | 6.7 | 6.3 | 5.8 | 5.4 |
| Thickness/fringe (Å/fg) | N/A | 428.2 | 455.4 | 494.7 | 531.3 |

Table 3 below shows similar results for the thin film wafers. More particularly, this table shows that the shortest wavelengths, which also provide the highest number of fringes (highest fringe frequency), may also provide for a better resolution of the wafer state. In this case, fringe analysis for the 315.6 nm wavelength estimates an in-situ deposition rate of 1394.3 Å/min as compared to the ex-situ measured deposition rate value of 1359.5 Å/min. Here, a comparison of averages shows that the average deposition rate is within 3% of the ex-situ measured deposition rate.

Comparison of Ex-Situ Measurements vs. In-Situ Estimates for Thin Film Wafers

TABLE 3

| Metrics | Ex-Situ | In-Situ | | | |
|---|---|---|---|---|---|
| | | 315.6 nm | 336.7 nm | 357.3 nm | 380 nm |
| Average Thickness (Å) | 1019.6 | N/A | N/A | N/A | N/A |
| Fringe Frequency (Hz) | N/A | 0.0547 | 0.0502 | 0.0468 | N/A |
| Deposition Rate (Å/min) | 1359.5 | 1394.3 | 1395.9 | 1403.4 | N/A |
| Standard Deviation (Å) | 8.14 | N/A | N/A | N/A | N/A |
| Number of Fringes | N/A | 2.4 | 2.2 | 2.04 | N/A |
| Thickness/fringe (Å/fg) | N/A | 424.8 | 463.5 | 499.8 | N/A |

Besides using the methods of the embodiments of the present invention to monitor a deposition or an etch process, the same methods are used in a production environment to control deposition or etch processes. For example, when it is desired to deposit a layer of silicon nitride with an approximate thickness of 2880 Å, the processor 118 counts 6.7 fringes at a wavelength of 315.6 nm and then stops the deposition process. The predetermined fringe count of 6.7 may be determined during a preproduction run and the count may be stored in memory of processor 118. Fractional fringe counts (e.g., 0.7) are determined by dividing a full fringe into segments and assigning a film thickness value to each such segment.

As will be understood by those of skill in the art, other equivalent or alternative methods for in-situ measuring of the etch rate or deposition rate and film thickness of a film being etched or deposited in a PECVD chamber according to the present invention can be envisioned without departing from the essential characteristics thereof. For example, the light detection equipment which is used to collect radiation reflected from the top and bottom of the film could be an interference filter and a photodiode to confine and detect the spectral composition of the plasma's optical emissions to a narrow detection interval. While embodiments of the present invention are described with respect to deposition processes, they are also applicable to etch processes, where the processor is able to determine an etched film thickness after having counted a predetermined number of plasma emission oscillations. These equivalents and alternatives along with obvious changes and modifications are intended to be included within the scope of the present invention. Accordingly, the foregoing disclosure is intended to be illustrative, but not limiting, of the scope of the invention which is set forth in the following claims.

What is claimed is:

1. A method for in-situ measurement of the film thickness of a non-opaque film on a substrate, said method comprising:
   forming a plasma to deposit or etch said film;
   collecting optical emissions, including those emitted from said plasma and reflected from said film on said substrate surface at grazing incidence;
   determining a rate of interference within the reflected light; and
   using said rate of interference to determine said film thickness.

2. The method of claim 1 wherein grazing incidence is an angle of at least 80 and less than 90 degrees as measured between an observation direction and a direction normal to said substrate surface.

3. The method of claim 1 further comprising using ex-situ measurements to obtain calibration data and performing said analyzing with said calibration data.

4. The method of claim 1 further comprising using an interference filter to confine the spectral composition of said optical emissions to an emission at a narrow spectral interval and a photodiode to detect said emission.

5. The method of claim 1 further comprising using the full spectral composition of said optical emissions and analyzing said interference fringes at a plurality of wavelengths.

6. The method of claim 1 wherein said rate of interference is correlated with a deposition rate.

7. A substrate processing system, said system comprising:
   a chamber having a chamber wall and a substrate support;
   and a window positioned in an opening of said chamber wall such that an angle between a center of said window and said substrate support is at least 80 and less than 90 degrees inclusive as measured with respect to a normal to said substrate support, said system configured to in-situ measure a film thickness of a non-opaque film being processed in said chamber, where being processed is being deposited or etched.

8. The substrate processing system of claim 7 further comprising:
an optical fiber, configured to be coupled with said window and configured to convey plasma emissions generated from a plasma source within said chamber;
a light detection device to detect a rate of interference caused by the interference of said plasma emissions reflected from a top and a bottom of a substrate surface placed within said chamber;
and a data analysis device configured to analyze said rate of interference to provide wafer state data, said system configured to in-situ measure a film thickness of a non-opaque film being processed in said chamber, where being processed is being deposited or etched.

9. A substrate processing system, said system comprising:
a chamber having a chamber wall and a substrate support;
a window positioned in an opening of said chamber wall such that an angle between a center of said window and said substrate support is at least 80 and less than 90 degrees inclusive as measured with respect to a normal to said substrate support;
an optical fiber configured to be coupled to said window and configured to convey plasma emissions generated from a plasma source within said chamber;
a light detection device to detect a rate of interference caused by the interference of said plasma emissions reflected from a top and a bottom of a substrate surface placed within said chamber;
and a data analysis device configured to analyze said rate of interference to provide wafer state data, said system configured to in-situ measure a film thickness of a non-opaque film being processed in said chamber, where being processed is being deposited or etched.

10. The system of claim 9 wherein said light detection device comprises an interference filter to confine the spectral composition of said optical emissions to an emission at a narrow wavelength band and a photodiode to detect said emission.

11. The system of claim 9 wherein said light detection device comprises a spectrometer to analyze the full spectral composition of said optical emissions at a plurality of wavelengths.

12. The system of claim 9 wherein the angle of incidence of said reflected optical emissions, measured between the observation direction and the direction normal to said substrate, is in a range of at least 80 and less than 90 degrees inclusive.

13. The system of claim 9 wherein said window is one of (a) a sapphire window or (b) a quartz window, and wherein said window is vertically mounted with its bottom edge placed above said substrate surface.

14. The system of claim 9 wherein said window is one of (a) a sapphire window or (b) a quartz window, and wherein said window is vertically mounted with its bottom edge placed above said substrate surface and its top edge placed below an upper electrode of said chamber.

15. The system of claim 9 wherein said optical fiber is mounted perpendicular to said window, and where no optical lens devices are placed between said window and said optical glass fiber.

16. The system of claim 9 wherein said wafer state data comprises fringe frequency, film thickness per fringe, total film thickness, deposition rate, and etch rate.

17. A method for in-situ control of the deposition of a non-opaque film on a substrate, said method comprising:
forming a plasma;
depositing said film using said plasma;
while depositing the film, collecting optical emissions from said plasma reflected from said film at a grazing incidence angle of at least 80 and less than 90 degrees and counting periodic oscillations in plasma emissions caused by the interference of plasma emissions reflected from a top and a bottom of said film; and
stopping the deposition of said film once a predetermined oscillation count is reached.

18. A method for in-situ control of the etching of a non-opaque film on a substrate, said method comprising:
forming a plasma;
etching said film using said plasma;
while etching the film, collecting optical emissions from said plasma reflected from said film at a grazing incidence angle of at least 80 and less than 90 degrees and counting periodic oscillations in plasma emissions caused by the interference of plasma emissions reflected from a top and a bottom of said film; and
stopping the etching of said film once a predetermined oscillation count is reached.

19. The method of claim 17 wherein the collected optical emissions are decomposed into spectral components using a spectrometer.

20. The method of claim 17 wherein the collected optical emissions are passed through an interference filter to confine an emission to a narrow wavelength interval and then delivered to a photodiode to detect the intensity of the confined emission.

21. The method of claim 17 wherein the optical emissions are reflected from the chamber into a fiber optic cable operatively coupled to a window in the chamber.

22. The method of claim 18 wherein the collected optical emissions are decomposed into spectral components using a spectrometer.

23. The method of claim 18 wherein the collected optical emissions are passed through an interference filter to confine an emission to a narrow wavelength interval and then delivered to a photodiode to detect the intensity of the confined emission.

24. The method of claim 18 wherein the optical emissions are reflected from the chamber into a fiber optic cable operatively coupled to a window in the chamber.

* * * * *